United States Patent [19]

Yeoman et al.

[11] Patent Number: 4,916,055
[45] Date of Patent: Apr. 10, 1990

[54] DETECTION OF HUMAN CANCER WITH A MONOCLONAL ANTIBODY SPECIFIC FOR ANTIGEN GP650

[75] Inventors: Lynn C. Yeoman, Houston, Tex.; Joseph P. Moosic, Arlington Heights, Ill.

[73] Assignee: Baylor College of Medicine, Houston, Tex.

[21] Appl. No.: 808,910

[22] Filed: Dec. 13, 1985

[51] Int. Cl.$^4$ .................. G01N 33/53; G01N 33/577; C07K 1/14; C12N 1/00
[52] U.S. Cl. ..................................... 435/7; 435/172.2; 435/240.27; 435/803; 435/810; 436/501; 436/548; 436/808; 436/813; 530/350; 530/387; 530/413; 530/417; 935/108; 935/110
[58] Field of Search .................... 435/7, 172.2, 240.27, 435/803, 810; 436/548, 811, 813, 501, 536, 543, 544, 808; 530/350, 417, 387, 413; 935/108, 110, 106

[56] References Cited

U.S. PATENT DOCUMENTS

| 4,444,744 | 4/1984 | Goldenberg | 424/1.1 |
| 4,628,032 | 12/1986 | White et al. | 530/387 |
| 4,699,877 | 10/1987 | Cline et al. | 530/387 |

OTHER PUBLICATIONS

Chakrabarty et al., Chemical Abstract, No. 862936, 1983.
Goldenberg et al., Cancer Research, vol. 36, 1976, pp. 3455–3463.
Chakrabarty et al., Journal of Immunological Methods, vol. 43, 1981, pp. 301–311.
Lehninger, Biochemistry, Second Edition, The Molecular Basis of Cell Structure and Function, Worth Publishers, Inc., 1975, p. 141.
Moosic et al., Federation Proceedings, vol. 44, No. 3, Mar. 1, 1985, No. 2229.
Sevier et al., Clin. Chem., vol. 27/11, 1981, pp. 1797–1806.
Abnormal Pattern of Mucus–associated M1 Antigens in Histologically Normal Mucosa Adjacent to Colonic Adenocarcinonas, J. Bara, J. Andre, R. Gautier, & P. Burtin, Cancer Research, vol. 44, pp. 4040–4045, Sep. 1984.
Isolation and Partial Characterization of a 700 Kilodalton Human Colon Carcinoma Associated Antigen, S. Chakrabarty, C. W. Taylor and Lynn C. Yeoman, Cancer Biochem. Biophys., 1983, vol. 6, pp. 249–259.
An Enzyme Immunoassay for the Detection of Human Tumor Nucleolar Antigens, David E. Kelsey, Rose K. Busch and Harris Busch, Cancer Letters, 12, (1981), pp. 295–303.
Identification of Cytosoltic Antigens from GW–39 Adenocarcinoma Cells by Crossed Immunoelectrophoresis and Immjunofluorescence, Charles W. Taylor, Subhas Chakrabarty, Keith S. Schauder, and Lynn C. Yeoman, Immunological Communications, 12(3), pp. 315–329 (1983).

*Primary Examiner*—David M. Naff
*Assistant Examiner*—Florina B. Hoffer
*Attorney, Agent, or Firm*—Fulbright & Jaworski

[57] ABSTRACT

A specific high molecular weight antigen (gp650) is detected in the sera of cancer patients with gastrointestinal cancer, cancer of the liver, breast cancer, cancer of the lung, cancer of the tongue, fallopian cancer, lymphoma and multiple myeloma. A monoclonal antibody specific for the 650 kD high molecular weight glycoprotein antigen has been harvested from mouse ascites and culture supernatants and used for the detection of antigen in cancer patient sera. Disclosed are (1) the method for preparing the antigen, (2) the properties of the antigen, (3) the method for preparation of the monoclonal antibody, (4) the characteristics and specificity of the monoclonal antibody and (5) a diagnostic kit based upon the specific monoclonal antibody.

13 Claims, 1 Drawing Sheet

DETECTION OF HUMAN CANCER WITH A MONOCLONAL ANTIBODY SPECIFIC FOR ANTIGEN GP650

FIELD OF THE INVENTION

This invention enables detection of elevated levels of high molecular weight antigen gp650 in the sera of patients with gastrointestinal cancer, hepatoma, cancer of the breast, cancer of the lung, cancer of the tongue, fallopian cancer, lymphoma and multiple myeloma. Normal human serum and serum from patients with some other cancers had low or undetectable levels of this antigen.

BACKGROUND OF THE INVENTION

Earlier studies utilizing polyclonal antibodies and immunofluorescence (Goldenberg et al., Cancer Res. 36, 3455, 1976; Chakrabarty et al., J. Immunol. Methods, 43, 301, 1081; Taylor et al., Immun. Commun., 12, 315, 1983; Chakrabarty et al., Cancer Biochem. Biophys. 6, 249, 1983) showed that the cytosol fraction from the GW-39 tumor (a human/hamster xenograft) was a source of antigens expressed by a number of primary human colon tumors. Indirect immunofluorescence studies (Hilgers et al., Cancer Res. 32, 98, 1972) on human colon tumor cryosections using these polyclonal antisera and those of others (Arends et al., Biochim. Biophys. Acta 780, 1, 1985) have demonstrated moderate to bright immunofluorescence in many specimens obtained from human cancers of the bowel (Yeoman et al., Meth. in Cancer Res. 19, 233, 1982). Crossed immunoelectrophoretic analyses (Laurell, Scand. J. Clin. Lab. Invest. 29, 21, 1972) had shown that these polyclonal antisera were capable of recognizing more than 20 antigens (Chakrabarty et al., 1983). After extensive preabsorptions were performed with normal human and normal hamster tissues, only three antigens were detected. Using a quantitative filter-based radioimmunoassay (Chakrabarty et al., 1983), it was shown that elevated levels of colon antigen 3 (CA-3) expression could be measured in the extracts of primary human colon tumors but that negative or low levels were detected in the extracts of normal colon mucosa and the mucosa removed from nontumorous colon samples (Bara et al., Cancer Res. 44, 4040, 1984). Further biochemical characterization of the antigens recognized by these sera showed that they had molecular weights of 600–800 kilodaltons (Chakrabarty et al., 1983).

Inasmuch as quantitative data obtained with polyclonal antisera had indicated that immunoassays based upon reactivity with antigens of very high molecular weight could discriminate between samples of colon cancers, normal adjacent colon and normal colon specimens, the present inventors began experiments in which selected immunizations were done with antigens of high molecular weight (600–800 kilodaltons). The present invention has resulted from studies designed to produce monoclonal antibodies to human tumor antigens of high molecular weight and to detect their presence in peripheral blood specimens. The advantages of monoclonal antibodies over the polyclonal antibodies used in the previous studies are: (1) the high specificity of monoclonal antibodies (2) the potentially unlimited supply of antibody and (3) the absence of a need for absorptions to improve their specificity. The advantages of a serum based test over the assay of extracts prepared from tumor specimens are: (1) the ease of sample acquisition, (2) the ability to screen for cancer in patients at high risk for specific types of cancer and (3) the possibility of early detection in asymptomatic individuals and (4) the ability to subsequently follow therapy or reoccurrence of disease.

Antigen gp650 has a molecular weight of approximately 650 kD as determined by gel filtration on a calibrated S-300 Sephacryl column and has been shown by immunofluorescence to be localized within the cytoplasm of human colon tumor cells that express this antigen.

The following Table 1 presents a summary of the characteristics of antigen gp650. The antigenic determinant recognized by the monoclonal antibody is on this protein and is distinct from carcinoembryonic antigen (CEA) with regard to its immunoreactivity and its chromatographic behavior (Kessler et al., Cancer Res. 38, 1041, 1978).

In Table 2, the clinical specificity of the monoclonal antibody is shown. Elevated levels (Table 3) of gp650 were found in the sera of patients with gastrointestinal cancers, cancers of the breast, cancer of the lung, cancer of the tongue, fallopian cancer, lymphoma, hepatomas and multiple myelomas. Normal human serum and primary biliary cirrhosis sera did not have elevated levels of gp650.

TABLE 1

Properties[a] of Human Cancer Antigen gp650

650 kilodalton molecular weight (native)
300 kilodalton molecular weight (denatured)
Glycoprotein
Cytosolic in origin and localization
In serum of cancer patients
Protein determinant
Derived from high molecular weight fraction of GW-39 tumor cytosol (human/hamster xenograft)
Destroyed by trypsin, pronase, $HNO_2$ and 2-mercaptoethanol
Immunologically and chromatographically distinct from CEA (carcinoembryonic antigen)
Insensitive to treatment with chondroitinase ABC, endoglycosidase
H, mixed endoglycosidases and DNase I

[a]Molecular weights were determined by gel filtration on a calibrated Sephacryl S-300 column in the presence (denatured) and absence (native) of 8 M guanidine-hydrochloride. Antigen gp650 was treated with proteases, endoglycosidases, nitrous acid, reducing agent, chondroitinase ABC and DNase I to determine its composition, sensitivities and insensitivities. The gel filtration characteristics of carcinoembryonic antigen were determined by ELISA assay using a commercial antiserum.

TABLE 2

Clinical Specificity[a] of the Monoclonal Antibody Specific for Antigen gp650

| Cancer | Specimens |
| --- | --- |
| gastrointestinal | 8/9 |
| breast | 4/4 |
| hepatoma | 3/3 |
| multiple myeloma | 2/2 |
| lymphoma | 1/2 |
| lung | 1/1 |
| fallopian | 1/1 |
| tongue | 1/1 |
| uterine | 0/1 |
| prostate | 0/1 |
| esophagus | 0/1 |
| Non-cancer | |
| normal serum | 0/3 |

TABLE 2-continued

Clinical Specificity[a] of the Monoclonal Antibody Specific for Antigen gp650

| Cancer | Specimens |
| --- | --- |
| primary biliary cirrhosis | 0/1 |

[a]Immunoreactivity was determined by a direct binding ELISA assay using antigen bound to plastic microtiter plates. Following incubation with primary antibody, a horse antimouse biotinylated second antibody was added followed by an avidin-biotinylated horseradish peroxidase complex. Immunoreactivity was measured by quantitating the amount of bound horseradish peroxidase with the addition of 2,2'-azino-di-(3-thylbenzthiazolinsulfonat(6)) diammonium salt (ABTS) and hydrogen peroxide followed by the development of color (Kelsey et al., Cancer Letters 12,295, 1981).

TABLE 3

Quantitative Immunoreactivity[a] of Human Serum Specimens with a Monoclonal Antibody to Human Cancer Antigen gp650

| Specimens | Number of Samples | Units[b] of Immunoreactivity Range[c] | Mean |
| --- | --- | --- | --- |
| Cancers: | | | |
| hepatoma | 3 | 14–75 | 39 |
| lung | 1 | 30 | 30 |
| breast | 4 | 10–45 | 30 |
| fallopian | 1 | 29 | 29 |
| myeloma, multiple | 2 | 8–32 | 20 |
| colon | 9 | 0–45 | 16 |
| tongue | 1 | 6 | 6 |
| lymphoma | 2 | 0–10 | 5 |
| uterus | 1 | 4 | 4 |
| prostate | 1 | 0 | 0 |
| esophagus | 1 | 0 | 0 |
| Non-cancers: | | | |
| normal serum | 3 | 2 | 2 |
| primary biliary cirrhosis | 1 | 2 | 2 |

[a]Immunoreactivity was determined by the direct binding ELISA method described in the legend to Table 2.
[b]The Units are expressed in ng of S-300 Sephacryl purified gp650 per ul of serum.
[c]Values are based upon a minimum of triplicate analyses.

SUMMARY OF THE INVENTION

The present invention resides in the discovery that a high molecular weight antigen (gp650) is found in the sera of patients diagnosed as having cancer of the gastrointestinal tract, cancer of the breast, cancer of the liver, cancer of the lung, cancer of the tongue, fallopian cancer, lymphoma and multiple myeloma. In the sera of patients with other types of cancer, patients with primary biliary cirrhosis and sera from normal individuals the levels of antigen were low or the antigen was absent. Important aspects of the invention are: discovery of a common antigen in sera of cancer patients, isolation and purification of antigen gp650, production of a monoclonal antibody specific to this antigen, a diagnostic test using the monoclonal antibody specific to this antigen and a diagnostic kit containing monoclonal antibody specific to human cancer antigen gp650.

Accordingly, an object of the present invention is the provision of cytosolic antigen gp650 which is present in cytoplasmic extracts of GW39 tumor cells and found in sera from patients with a range of cancers.

A further object of the present invention is the provision of a monoclonal antibody specific to antigen gp650 which can be used for diagnostic and treatment purposes.

A further object of the present invention is the provision of this cytosolic antigen in purified form.

A further object of the present invention is the provision of the processes for extracting and isolating the purified antigen gp650.

A further object of the present invention is the provision of a diagnostic kit comprised of monoclonal antibody specific to human cancer antigen gp650.

A further object of the present invention is the provision of a monoclonal antibody specific to the human cancer antigen gp650 which serves as a carrier for markers for diagnostic purposes.

Other and further objects, features and advantages of the invention appear throughout.

DESCRIPTION OF THE PREFERRED EMBODIMENTS

Figure 1:
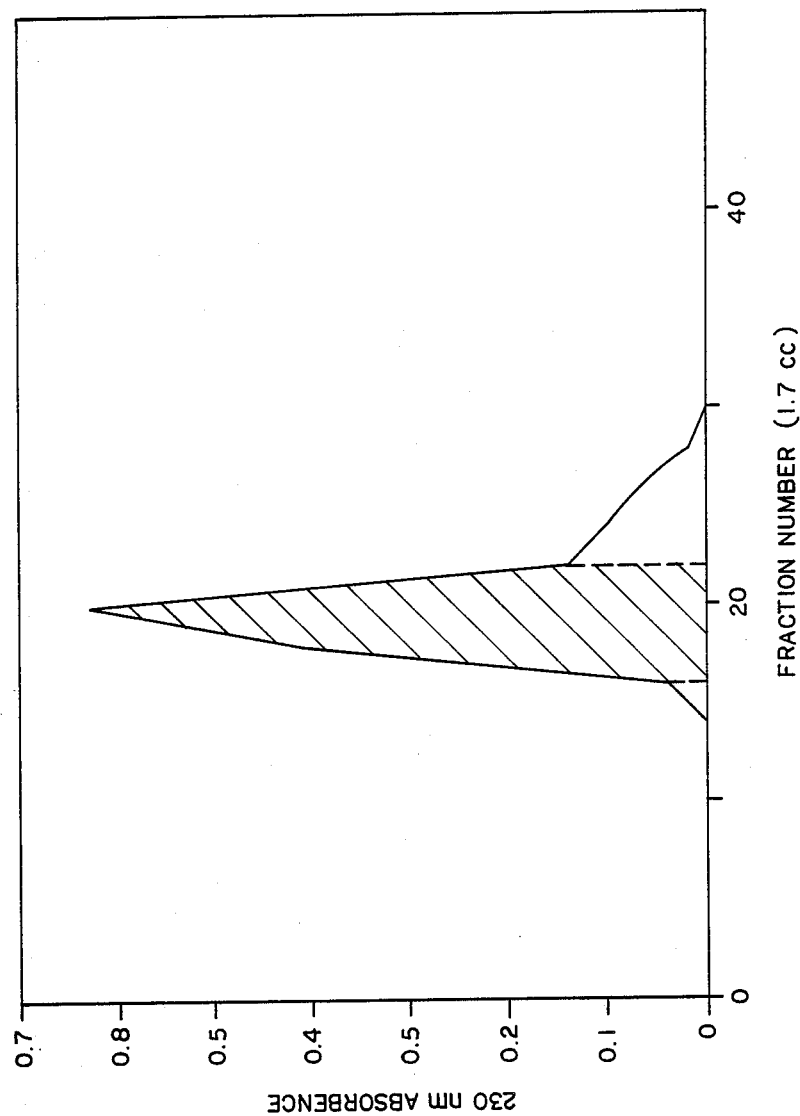
FIG. 1 is S-300 Peak 1 recomatagraph on Sephacryl S-300 rechromatography of the human cancer antigen gp650. The shaded region corresponds to fractions that were pooled and concentrated.

The present invention resides in the discovery that a common human cancer antigen gp650 is present in the sera of patients with a range of human cancers, the extraction, isolation and partial purification, the production of a monoclonal antibody of high speificity and selectivity to this antigen which can be tagged directly or indirectly to permit diagnostic testing for human cancers in vitro and in vivo.

The Human Cancer Antigen gp650

The human cancer antigen gp650 has been found at elevated levels in the sera of human cancer patients with gastrointestinal cancer, cancer of the breast, cancer of the liver, cancer of the lung, cancer of the tongue, fallopian cancer, lymphoma and multiple myeloma. The largest numbers of specimens analyzed exhibiting elevated levels of the gp650 antigen were from patients with cancer of the colon, cancer of the breast and cancer of the liver. The antigen is obtainable from the cytoplasm of human colon tumor cells and body fluids containing such antigens.

The antigen is either absent or present at low levels in the sera of normal individuals, in patients with primary biliary cirrhosis and with cancers of the prostate, uterus and esophagus.

The human cancer antigen gp650 is identified by exclusion chromatography as a 650 kilodalton antigen molecule under native conditions. A 300 kilodalton antigen was obtained by gel filtration of gp650 in the presence of 8 M guanidine-hydrochloride. Immunocytochemical studies have shown that the antigen is localized in the cytoplasm of colon cells that contain the antigen.

Human cancer antigen gp650 is extractable from GW39 tumor cells by homogenization in 0.05 M Tris buffer (pH 7.4) containing 0.005 $MgCl_2$, 0.025 M KCl, 1 mM phenylmethanesulfonyl fluoride and 0.1 mM leupeptin. Following centrifugation at 100,000 x g for 4 hours, the antigen remains in the soluble, cytosolic fraction. The human cancer antigen gp650 has been highly purified by selective extraction, by chromatography on Sephadex G-100 columns and by two passages over a Sephacryl S-300 column. Upon rechromatography, the antigen elutes as a single symmetrical peak with a molecular weight of approximately 650 kilodaltons (FIG. 1).

This antigen is detected at very low levels. in sera of normal individuals.

Human Sera

All steps involved in the collection and analysis of human sera and tissues were approved by the Baylor Institutional Review Board for Human Research. Patient sera were collected from patients mainly from the gastroenterology and oncology services at The Methodist Hospital and the Ben Taub Hospital, Houston, Tex. Sections of human tumors were procured from the University of Alabama Tissue Procurement Program in Birmingham, Ala. Cryostat specimens were prepared by the Department of Pathology at Baylor College of Medicine.

Preparation of GW-39 Cell Cytosol

GW-39 solid tumors were surgically removed from the hind flank of Golden Syrian Hamsters (Goldenberg et al., 1976) and ground in a Hobart meat grinder and dispersed in 10 volumes of Modified Eagle's medium containing 10% fetal calf serum and 0.05% neuraminidase. The suspension was agitated gently at 37° C. for 3 hours. The cell clusters were collected by centrifugation at 1000 x g for 20 minutes. The cell clusters were washed two times by suspension in reticulocyte standard buffer (RSB=0.01 M Tris-HCl/0.01 MNaCl/1.5 mM Mg acetate, pH 7.4) containing 1 mM phenylmethanesulfonyl fluoride and 0.1 mM leupeptin and centrifuged at 1000 x g for 10 minutes. The washed tumor cells were suspended in 0.05 M Tris-HCl/0.005 M $MgCl_2$/0.025 M KCl (pH 7.4) containing 1 mM phenylmethanesulfonyl fluoride and 0.1 mM leupeptin and homogenized with a SD-45 Super Dispax until most nuclei were released freed of cytoplasm. Cell breakage was monitored by phase contrast microscopy. Unbroken cells and nuclei were removed by centrifugation at 1000 x g for 20 minutes and the cytoplasmic supernatant was collected. Cytosol was prepared from the crude cytoplasmic fraction by sequential centrifugations at 10,000 x g for 20 minutes and 100,000 x g for 4 hours.

Preparation of Antigen gp650 for Immunization

The cytosol fraction was concentrated to 10 mg protein/ml in a stirred pressure dialysis cell and 200 mg were loaded on a G100 Sephadex column. The excluded volume fraction was collected, concentrated to 5 mg/ml and 10 mg were loaded on a S-300 Sephacryl column. The high molecular weight fraction eluting at a molecular weight of approximately 650 kD was collected, concentrated and 4 mg were rechromatographed on a S-300 Sephacryl column (FIG. 1). The single, Virtually symmetrical peak was collected and analyzed for low molecular weight components by discontinuous buffer polyacrylamide gel electrophoresis (Laemmli, 1970) and shown to be free of peptides with molecular weights less than 250 kilodaltons as analyzed by silver staining. Composite gel analysis on agarose/acrylamide gels revealed a slow moving broad region of silver stainable and antibody blot detectable material. The 650 kD material from repeated S-300 Sephacryl chromatography runs was used for the immunization of mice.

Immunization and Development of Monoclonal Antibodies

Four to six week old female Balb/c mice were given 4 injections i.p. of 650 kD antigen. The initial injection used 430 ug of antigen in complete Freund's adjuvant. One month after the primary injection the mice were given a series of three booster injections in incomplete Freund's adjuvant at 6 week intervals. The mice were sacrificed and the spleen cells were collected for fusion 2-4 days after the final booster immunization.

Cell Fusion and Cloning

Lymphocytes from female Balb/c mouse spleens were collected from Ficoll-Hypaque gradients (M.A. Bioproducts, Walkersville, Md.) and fused with P3-X63-Ag8.653 myeloma cells (Salk Institute, San Diego, Calif.) in 1 ml of a 50% polyethylene glycol solution (PEG 1500) (Hybridoma Science) in Dulbecco's modified Eagle's medium (DMEM) for 15 minutes. Cells were collected by centrifugation at 500 x g for 15 minutes. The cells were resuspended in hybridoma media (Dulbecco's modified Eagle's medium containing 20% fetal calf serum, 2 mM glutamine, 100 units penicillin, 100 units streptomycin, 1 mM sodium pyruvate, modified Eagle's medium nonessential amino acids with 14 $\mu$M thymidine/0.1 mM hypoxanthine/0.4 $\mu$M aminopterin. The cell suspension was aliquoted into four 24 well culture plates containing 1 x $10^6$ syngeneic spleen cells/well as a feeder layer.

Hybridoma Screening

When colonies were visible, the wells were screened for reactivity against native and 2-mercaptoethanol reduced immunogen using the dot immunoblot method (Bennett and Yeoman, 1983). Reactive hybridomas were subcloned by limited dilution in 96 well microtiter plates. Wells appearing to produce single colonies were retested by the dot immunoblot method. The recloned hybridomas were expanded into 24 well plates and into flasks without feeder layer cells. A hybridoma cell line that produces anti-gp650 has been deposited with the American Type Culture collection as ATCC HB 10238.

Growth of Hybridomas and purification of Monoclonal Antibodies

In order to produce large amounts of antibody at higher antibody concentration, the hybridoma clones were grown as ascites tumors as follows: approximately 1 x $10^6$ hybridoma cells were harvested from cell cultures and 5 x $10^5$ cells were injected i.p. in 0.5 ml of sterile phosphate buffered saline into mice that had been pretreated 10 days prior to injection with pristane (tetramethylpentadecane). After approximately one week of tumor growth, mice were tapped i.p. on alternate days and ascites fluid collected. Antibody was purified from ascites fluid by centrifugation. The monoclonal antibody was typed as an IgG1, k by the bound antigen method and by the goat anti-mouse method (IgG1 2a 2b, k). IgG fraction was purified from culture supernatants by ammonium sulfate precipitation and DEAE-Sephacel chromatography. Purified monoclonal antibody was aliquoted and stored at $-18°$ until used.

ELISA Assay of Human Cancer Antigen gp650 in Cancer patient Sera

Aliquots of cancer patient sera (1 $\mu$l and 5 $\mu$l) were diluted to 200 $\mu$l with Tris-buffered saline (TBS=0.05 M Tris-HCl/0.15 M NaCl/pH 7.4) and bound to the wells of a 96 well microtiter plate for 2 hours. This and all subsequent incubations and washes were done at 25° C. The wells were washed 4 times with TBS and blocked for 2 hours with TBS containing 3% bovine serum albumin and 10% chicken serum. Wells were washed once with TBS and the anti-gp650 monoclonal antibody was added at a 1:1000 dilution in blocking solution. After 2 hours the wells were washed four times with TBS and 200 μl of biotinylated horse antimouse antibodies (Vector Laboratories) were added at a 1:150 dilution in blocking solution containing 1% horse serum. After 1 hour the wells were washed 4 times with TBS and 200 μl of avidin-bound biotinylated horseradish peroxidase was added (Vector Laboratories) at a 1:500 dilution in TBS. Wells were washed 4 times with TBS and once with 0.05 M citrate/0.1 M phosphate (pH 4.0). Color was developed for 20 minutes with the addition of a freshly prepared color developing solution in 0.05 M citrate/0.1 M phosphate (pH 4.0) containing 0.02% hydrogen peroxide and 0.15 mg/ml ABTS reagent and read in an ELISA reader. Sample reactivity was calculated by subtracting the ELISA background obtained for clinical specimens assayed in the absence of anti-gp650 monoclonal antibody from the values obtained in the presence of primary antibody. Human cancer antigen gp650 ng equivalents were calculated from a standard curve based upon 50 to 500 ng amounts of S-300 Sephacryl purified antigen gp650; units were calculated as ng/μl equivalents.

Cancers that Exhibit High Serum Levels as Detected with the Test Antibody

These studies confirm that human cancer antigen gp650 is present in the sera at elevated levels in patients with gastrointestinal cancer, hepatoma, cancer of the breast, cancer of the lung, cancer of the tongue, fallopian cancer, lymphoma and multiple myeloma. Initial studies indicated the presence of human cancer antigen gp650 in cryosections prepared from human colon tumors and in cell cultures derived from human colon tumors. Normal individuals, patients with biliary cirrhosis and patients with other types of cancer had very low or undetectable levels of antigen in their sera.

EXAMPLE 1

Negative Sera—In five different types of specimens, 3 normal, 1 non-cancer and 3 types of cancer—the levels of human cancer antigen gp650 were undetectable or low (Table 3).

EXAMPLE 2

Background—Background levels derived from clinical serum specimens in the absence of anti-gp650 monoclonal antibody were variable; unknown substances may weakly bind elements of the second antibody and the biotinylated horseradish peroxidase or the second antibody and the biotinylated horseradish peroxidase detection system. This variability was compensated by subtraction of values obtained in the absence of the primary anti-gp650 monoclonal antibody from those obtained in its presence.

EXAMPLE 3

Antigen Range—The ELISA values that were obtained were converted to antigen units of ng/μl based upon a standard curve prepared from S-300 purified antigen. Values ranged from a low of 0 for cancer of the prostate and esophagus to a value of 75 for cancer of the liver. Values less than 2.5 were judged to be at or slightly above background. Values between 2.5 and 4.9 were evaluated as low. Values between 5 and 10 were evaluated as moderate and values above 10 were evaluated as high.

EXAMPLE 4

Cancers Other than Gastrointestinal Cancers—In addition to elevated levels of antigen gp650 in sera of patients with gastrointestinal cancer, moderate to high levels were also observed in sera from patients with cancer of the breast, liver, lung, tongue, fallopian tubes, myeloma and lymphoma. Low levels of gp650 were detected in the serum of patient with cancer of the uterus. Antigen gp650 was undetectable in sera of patients with prostate cancer and cancer of the esophagus.

EXAMPLE 5

Labeling—Direct immunochemical methods for the demonstration of the antibodies include labeling of the primary antibody with one or more of the following labels: a radioisotope for autoradiography or radioscintography such as $^{125}I$, $^{131}I$, $^{14}C$ or $^{3}H$: a fluorescent chromophore such as fluorescein, phycobiliprotein or tetramethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization.

Indirect—Indirect immunochemical methods include labelling the second antibody or other binding protein specific for the first antibody with a fluorophor dye, an electron dense compound, an enzyme which produces a product detectable by light, fluorescence or electron microscopic examination or a radioisotope detectable by autoradiography.

The indirect immunochemical methods for the visualization of the antibodies include application of hybrid primary or secondary antibodies or antibody fragments $(F(ab')_2)$ wherein part of the hybrid antibody preparation is specific for the human cancer antigen gp650, (hybrid primary antibody) or for the primary antibody (hybrid second antibody), and part is specific for a label, such as those mentioned in the preceeding paragraph.

DIAGNOSTIC KITS

Labelled, conjugated or nonconjugated antibody may be packaged in Tris buffered saline (TBS) or other buffered suspending agents for distribution. Suitable suspending agents include glycerin, heparin or sucrose. Suitable buffers include barbital buffers, morpholine buffers, MOPS-3-(N-morpholino) propane sulfonic acid, HEPES-N-2-hydroxyethylpiperazine-N-2-ethane sulfonic acid, phosphate, carbonate and the like.

The present invention, therefore, is well suited and adapted to attain the objects and ends described herein and has the features mentioned as well as others inherent therein.

While presently preferred embodiments of the invention have been given for purposes of the disclosure, changes can be made therein within the spirit of the invention as defined by the scope of the appended claims.

BACKGROUND REFERENCES

Arends, J. Bosman, F. T. and Hilgers, J. Tissue antigens in large-bowel carcinoma. Biochim. Biophys Acta 780 1-19, 1985.

Bara, J., Andre, J., Glautier, R. and Burtin, p. Abnormal pattern of mucus-associated M1 antigens in histologically normal mucosa adjacent to colonic adenocarcinomas. Cancer Res. 44: 4040-4045, 1984.

Bennett, P. C. and Yeoman, L. C. An improved procedure for the "dot immunobinding" analysis of hybridoma supernatants. J. Immun. Meth. 61: 201-207, 1983.

Chakrabarty, S., Taylor, C. W. and Yeoman, L. C. Comparison of immunoelectrophoretic techniques for the analysis of cytosol antigens. J. Immunol. Meth. 43: 301-311, 1981.

Chakrabarty, S., Taylor, C. W. and Yeoman, L. C. Isolation and partial characterization of a 700 kilodalton human colon carcinoma associated antigen. Cancer Biochem. Biophys. 6: 249-259, 1983.

Goldenberg, D. M., Witte, S. and Elster, K. GW-39: A new human tumor serially transplantable in the golden hamster. Transplant. 4: 760-763, 1976.

Goldenberg, D. M., pant, K. D. and Dahlman, H. L. Antigens Associated with Normal and Malignant Gastrointestinal Tissues. Cancer Res. 36: 3455-3463, 1976.

Hilgers, J., Nowinski, R. C., Geering, G. and Hardy, W. Detection of aviam and mammalian oncogenic RNA viruses (oncornaviruses) by immunofluorescence. Cancer Res. 32: 98-106, 1972.

Kelsey, D. E., Busch, R. K. and Busch, H. An enzyme immunoassay for the detection of human tumor nuoleclar antigens. Cancer Letters 12:295-303, 1981.

Kessler, M. J., Shively, J. E., pritchard, D. G. and Todd, C. W. Isolation, immunological characterization, and structural studies of a tumor antigen related to carcinoembryonic antigen. Cancer Res. 38, 1041-1048, 1978.

Laemmli U. K. Cleavage of structural proteins during the assembly of the head of bacteriophage T4. Nature (Lond.) 227:680-685, 1970.

Laurell, C. B. Electroimmunoassay. Scand. J. Clin. Lab. Invest. 29 (Suppl. 124): 21-37, 1972.

Taylor, C. W., Chakrabarty, S., Schauder, K. S. and Yeoman, L. C. Identification of cytosolic antigens from GW-39 adenocarcinoma cells by crossed immunoelectrophoresis and immunofluorescence. Immun. Comm. 12: 315-329, 1983.

Yeoman, L. C., Jordan, J. J., Busch, R. K., Taylor, C. W., Savage, H. and Busch, H. A fetal protein in the chromatin of Novikoff hepatoma and Walker 256 carcinosarcoma tumors that is absent from normal and regenerating rat liver. Proc. Natl. Acad. Sci. USA 73: 3258-3262, 1976.

Yeoman, L. C., Taylor, C. W. and Chakrabarty, S. Colon Tumor Antigens in, Vol. XIX of Methods in Cancer Research (H. Busch and L. C. Yeoman, Ed.) Academic press, N.Y., 1982, pp. 233-271.

We claim:

1. A human gp650 antigen being in substantially purified form, having:
    a molecular weight of about 650,000 daltons as determined by gel filtration on a calibrated S-300 Sephacryl column;
    a molecular weight of about 300,000 daltons after denaturation in the presence of 8M guanidine-hydrochloride;
    being soluble in 0.05 M Tris-HCl/0.005 M $MgCl_2$ 0.025 M KCl, pH 7.4; and;
    being primarily localized in the cytosolic fraction of human colon tumor cells.

2. A murine hybridoma which produces:
    a monoclonal antibody specifically immunoreactive with the gp650 antigen of claim 1.

3. A monoclonial antibody produced by the hybridoma of claim 2.

4. An immunological assay for detecting gp650 antigen in human serum, comprising:
    combining a monoclonal antibody of claim 3 with human serum; and
    assaying the human serum for antigen binding as a measure of a monoclonal antibody-gp650 antigen complex formed in said combining step;

5. The immunological assay of claim 4, wherein said complex contains a detectable label.

6. The immunological assay of claim 5 wherein said detectable lable is selected from the group consisting of radioactive material, fluorophor, dye, an electron dense compound and an enzyme.

7. The immunological assay of claim 4 wherein the antibody is detectably labeled.

8. The immunological assay of claim 4 wherein the antigen is detectably labeled.

9. A method for the immunological detection of cancer, comprising the steps of combining monoclonal antibodies to the gp650 antigen with a human serum sample; and
    measuring the amount of monoclonal antibody-gp650 antigen complex formed in the combining step, wherein elevated amounts of said complex indicate the presence of cancer.

10. The method of claim 9 wherein the detections of gp650 antigen is associated with cancers selected from the group consisting of hepatoma, gastoenestinal, breast, lung, tongue, fallopian lymphoma and multiple myeloma.

11. A method of purifying human cancer antigen gp650 from a sample including said antigen, comprising,
    sequential concentrating and purifying the antigen by a pressure dialysis cell concentration followed by Sephadex gel exclusion chromotography of the antigen, and repeated Sephacryl S-300 column exclusion chromotography of the antigen and recovering purified gp650 antigen.

12. The method of claim 11, further comprising the step of extracting said antigen from a cytosol fraction of human cancer cells.

13. A diagnostic kit suitable for detecting a gp650 antigen, comprising in containers:
    a monoclonal antibody specifically immunoreactive with a gp650 antigen.

* * * * *

UNITED STATES PATENT OFFICE
CERTIFICATE OF CORRECTION

Patent No. 4,916,055               Dated April 10, 1990

Inventor(s) Lynn C. Yeoman and Joseph P. Moosic

It is certified that error appears in the above-identified patent and that said Letters Patent is hereby corrected as shown below:

Column 5, line 25, change "MNaCl/1.5" to --M NaCl/1.5--
Column 5, line 51, change "Virtually" to --virtually-
Column 6, line 38, change "Hybridomas and purification" to --Hybridomas and Purification--
Column 6, line 59, change "Cancer patient sera" to --Cancer Patient Sera--
Column 8, line 18, change "$^3$H:" to --$^3$H;--
Column 8, line 65, change "Biophys" to --Biophys.--
Column 8, line 66, change "780" to --780:--
Column 8, line 67, change "Burtin, p." to --Burtin, P.--
Column 9, line 3, change "Bennett, P." to --Bennett, F.--
Column 9, line 18, change "Goldenberg, D.M., pant," to "Goldenberg, D.M., Pant,--
Column 9, line 27, delete "nuoleclar" and insert --nucleolar--
Column 9, line 28, change "pritchard, D.G." to --Pritchard, D.G.--
Column 9, line 52, change "Academic press" to --Academic Press--
Column 10, line 19, change "step;" to --step.--

Signed and Sealed this

Fourteenth Day of May, 1991

Attest:

HARRY F. MANBECK, JR.

*Attesting Officer*     Commissioner of Patents and Trademarks